(12) United States Patent
Onishi

(10) Patent No.: US 7,736,443 B2
(45) Date of Patent: Jun. 15, 2010

(54) ENDOSCOPE WASHER DISINFECTOR EQUIPPED WITH NOZZLE CONNECTABLE TO ENDOSCOPIC CHANNELS AUTOMATICALLY

(75) Inventor: Hideto Onishi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 343 days.

(21) Appl. No.: 11/964,840

(22) Filed: Dec. 27, 2007

(65) Prior Publication Data

US 2009/0090398 A1 Apr. 9, 2009

(30) Foreign Application Priority Data

Dec. 27, 2006 (JP) ............................. 2006-353393

(51) Int. Cl.
*B08B 9/00* (2006.01)
(52) U.S. Cl. .................. 134/167 C; 134/170; 134/171; 134/169 R; 134/166 C; 239/267; 239/54; 239/266; 239/269; 222/148
(58) Field of Classification Search ............. 134/167 C, 134/170, 171, 169 R, 166 C; 239/267, 541, 239/266, 269; 222/148
See application file for complete search history.

(56) References Cited

U.S. PATENT DOCUMENTS 6,041,794 A 3/2000 Lin et al.

2005/0209507 A1* 9/2005 Suzuki et al. ............... 600/133

FOREIGN PATENT DOCUMENTS

| EP | 1 728 465 A1 | 12/2006 |
| EP | 1 728 466 A2 | 12/2006 |
| JP | 2000-300515 | 10/2000 |

\* cited by examiner

*Primary Examiner*—Michael Cleveland
*Assistant Examiner*—Samuel A Waldbaum
(74) *Attorney, Agent, or Firm*—Scully, Scott, Murphy & Presser, P.C.

(57) ABSTRACT

In an endoscope washer disinfector, a bath comprises a mounting plane on which an endoscope with a duct is mounted and a wall member. A connector has two ends consisting of one end located to penetrate through the wall member and to be secured watertightly to the wall member. The one end faces an opening of the duct of the endoscope mounted in the bath. The other end is connected to a fluid source storing fluid for washing and disinfecting the endoscope. A nozzle is movable in the connector along an inner passage thereof and moved toward the one end of the connector to protrude from the one end to realize a watertight and detachable connection with the opening of the duct. The fluid is supplied to the duct when the fluid is supplied from the fluid source.

10 Claims, 8 Drawing Sheets

ENDOSCOPE WASHER DISINFECTOR EQUIPPED WITH NOZZLE CONNECTABLE TO ENDOSCOPIC CHANNELS AUTOMATICALLY

CROSS REFERENCE TO RELATED APPLICATION

The present application relates to and incorporates by reference Japanese Patent application No. 2006-353393 filed on Dec. 27, 2006.

BACKGROUND OF THE INVENTION

1. Field of the Invention

The present invention relates to an endoscope washer disinfector for washing and disinfecting used endoscopes, and in particular, to an endoscope washer disinfector equipped with a nozzle to supply fluid to endoscopic channels in such a manner that the nozzle is connected automatically to the openings of the channels.

2. Related Art

A medical endoscope is equipped with an elongated flexible insertion tube to be inserted into patients' body cavities so that organs and tissue in the cavities can be visually observed and various types of endoscopic therapy can be conducted. For the endoscopic therapy, desired therapeutic instruments are inserted through a therapeutic channel of the insertion tube. Once the insertion tube is inserted into a patient's body cavity, the surfaces of the insertion tube are subjected to adherence of contamination from body fluids such as mucous membrane, blood, and waste materials. Thus it is always necessary to sufficiently wash and disinfect the used endoscopes. For washing and disinfecting endoscopes, an apparatus for washing and disinfecting endoscopes, which is called an endoscope washer, is used. A used endoscope to be washed and disinfected is accommodated in the washing/disinfecting bath (simply, washing bath) of the endoscope washer disinfector, and then subjected in sequence to necessary various processes including wash, disinfection, rinse, and drying processes.

The endoscopic channels, which are ducts formed through the insertion tube, consist of a plurality of channels such as an air-supply water-supply channel and a therapeutic-instrument channel. These channels, in particular, the inside thereof should be subjected to sufficient passage of washing and disinfecting liquid agents for reliable wash and disinfection.

As such an endoscope washer disinfector which has the capability of washing and disinfecting the outer surfaces of endoscopes and the inner channels thereof, an apparatus disclosed by Japanese Patent Laid-open Publication No. 2005-270142 is known.

This conventional endoscope washer disinfector is equipped with a duct joint portion to move toward an endoscope channel. This duct joint portion can be connected automatically to the channel by an electrically operated mechanism driven on an electric motor. With the connection realized, liquid agents such as washing and disinfecting agents, which circulate in the washer disinfector, are fed through the channel for wash and disinfection.

However, in the endoscope washer disinfector disclosed by the above publication, it is necessary to control electrical components including the motor to drive the duct joint portion. Further, the disclosed washer disinfector is structured such that the duct joint portion slides on part of the washing bath. It is thus necessary to hold a watertight performance at the sliding portion by adopting sealing members, such as an O-ring, on the part of the washing bath. It is therefore inevitable to avoid deterioration of the sealing members due to frication with the movable duct joint portion. A higher deterioration may cause the liquid in the washing bath to leak into the main body of the washer disinfector. When such a leakage occurs, the various electrical and mechanical components may be damaged or troubled.

SUMMARY OF THE INVENTION

The present invention has been made in consideration of the above drawbacks, and an object of the present invention is to provide an endoscope washer disinfector in which a nozzle to supply fluids necessary for washing and disinfecting endoscopes can be detachably connected to endoscopic channels with a simplified, reliable, and watertight connection structure.

The present invention provides an endoscope washer disinfector comprising: a bath comprising a mounting plane on which an endoscope provided with a duct necessary for endoscopic therapy is mounted and a wall member that surrounds the mounting plane, wherein the mounting plane provides a given position at which the endoscope is positioned; a connector having i) two ends consisting of one end located to penetrate through the wall member and to be secured watertightly to the wall member such that the one end faces an opening of the duct of the endoscope mounted at the given position in the bath and the other end receiving fluid for washing and disinfecting the endoscope and ii) an inner passage that communicates between both ends; and a nozzle inserted watertightly and movably in the connector along the inner passage thereof and moved toward the one end of the connector to protrude from the one end to realize a watertight and detachable connection with the opening of the duct so as to supply the fluid to the duct when the fluid is supplied from the fluid source.

Thus, in the endoscope water disinfector according to the present invention, by combining the nozzle with the connector, it is possible to simplify, in a reliable manner, the structure of connection of the nozzle to the channels (ducts) of a used endoscope accommodated in the bath and, also to secure a sufficient watertight performance between the bath and the nozzle.

DETAILED DESCRIPTION OF THE PREFERRED EMBODIMENTS

First Embodiment

Referring to FIGS. 1-11, an endoscope washer disinfector 1 (i.e., an apparatus for washing and disinfecting used endoscopes) according to a first embodiment of the present invention will now be described.

Figure 1:
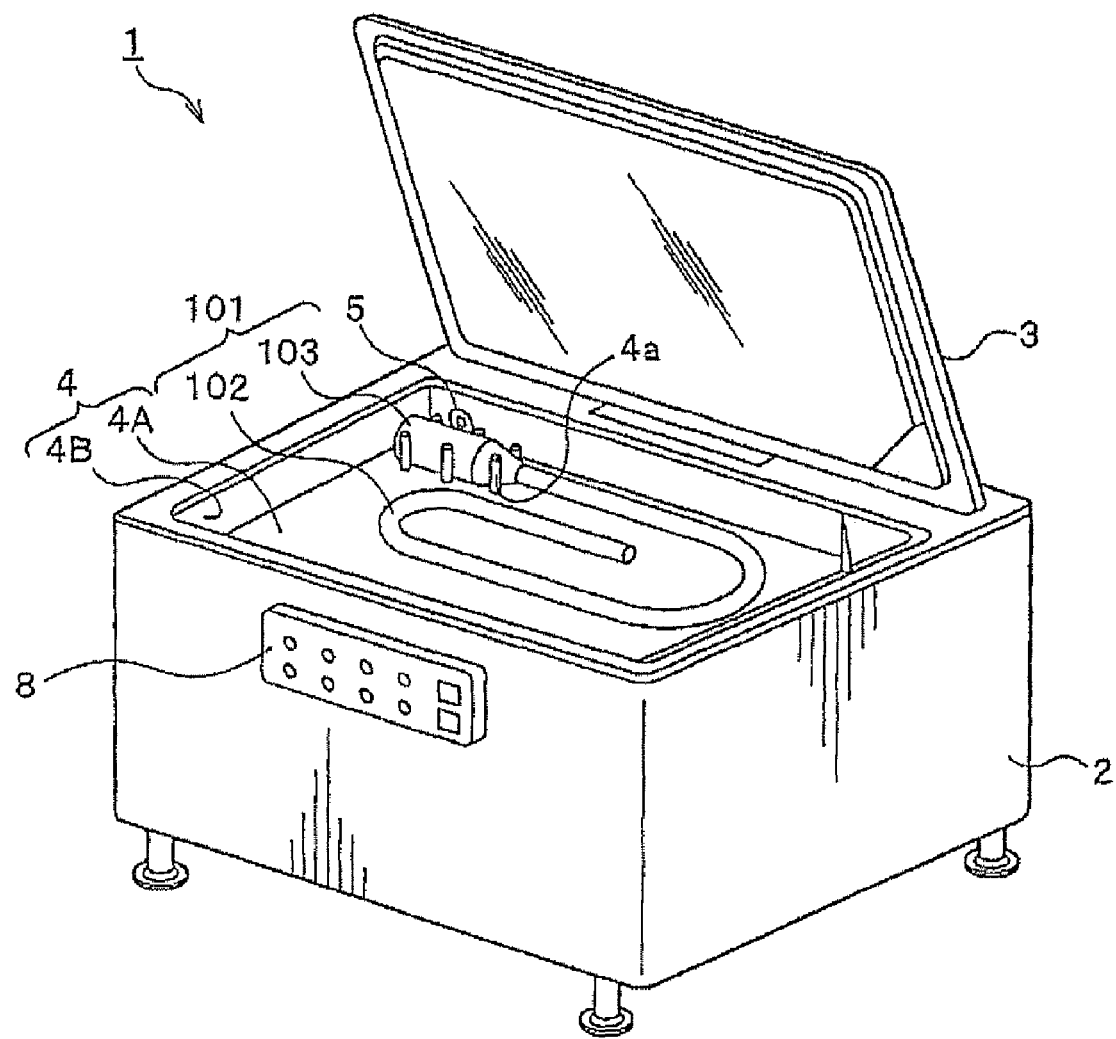
FIG. 1 is a perspective view showing an endoscope washer disinfector according to an embodiment of the present invention.

As shown in FIG. 1, the endoscope washer disinfector 1 comprises a apparatus main body (or simply "main body") 2 produced into an approximately box-like shape as a whole and a top cover 3 to cover the top face of the apparatus main body 2. The top cover 3, which functions as a cover for a washing/disinfecting bath, is attached to an edge of the top face of the apparatus main body 2 using a hinge device (not shown) so as to open and close the top face of the apparatus main body 2.

At an upper part of the apparatus main body 2, there is produced a washing/disinfecting bath 4 (hereinafter, simply referred to as "washing bath") so as to open upward, in which a used endoscope 101 can be accommodated. The endoscope accommodated in the washing bath 4 is subjected to processes for washing and disinfection on predetermined washing/disinfection procedures. In such processes, the top cover 3 is closed to cover the washing bath 4. On the front of the apparatus main body 2, an operation panel 8 is provided. This operation panel 8 is provided with operation devices which allow an operator to enter various settings and instructions to the washer disinfector as well as display devices for displaying various pieces of information. Such operation and display devices are electrically connected to internal electrical circuitry.

The endoscope 101 comprises a flexible insertion tube to be inserted into patient's body cavities and a manipulating device 103 which is grasped by an operator, such as a doctor, for manipulating the endoscope. The insertion tube is bent in an approximately spiral form and disposed in a given mounting position on a bottom 4A of the washing bath 4. Specifically, the manipulating device 103 is almost fixedly located between plural pins 4a standing from the washing-bath bottom 4A. At a given position of a side wall 4B of the washing bath 4, which position is exposed to the inside of the bath 4 is near to the positioned manipulating device 103, there is provided a fluid discharge device 5 to appear from the side wall 4B. By the way, other pins can be arranged on the bath bottom 4A to position the insertion tube 120 in a predetermined form.

The fluid discharge device 5 comprises a mechanism for connecting a supply pipe to the openings of various endoscopic channels (i.e., ducts) of the endoscope 101 in an automatic and detachable manner. Various types of fluid, such as washing agent, disinfecting agent, and alcohol, is supplied to the supply pipe, which is formed as a nozzle NZ which is one of the essential members of the device 5. The endoscopic channels are opened outside from the manipulating device 103. Thus, as will be detailed later, the nozzle NZ is detachably and watertightly connected to the openings of the channels.

Figure 2:
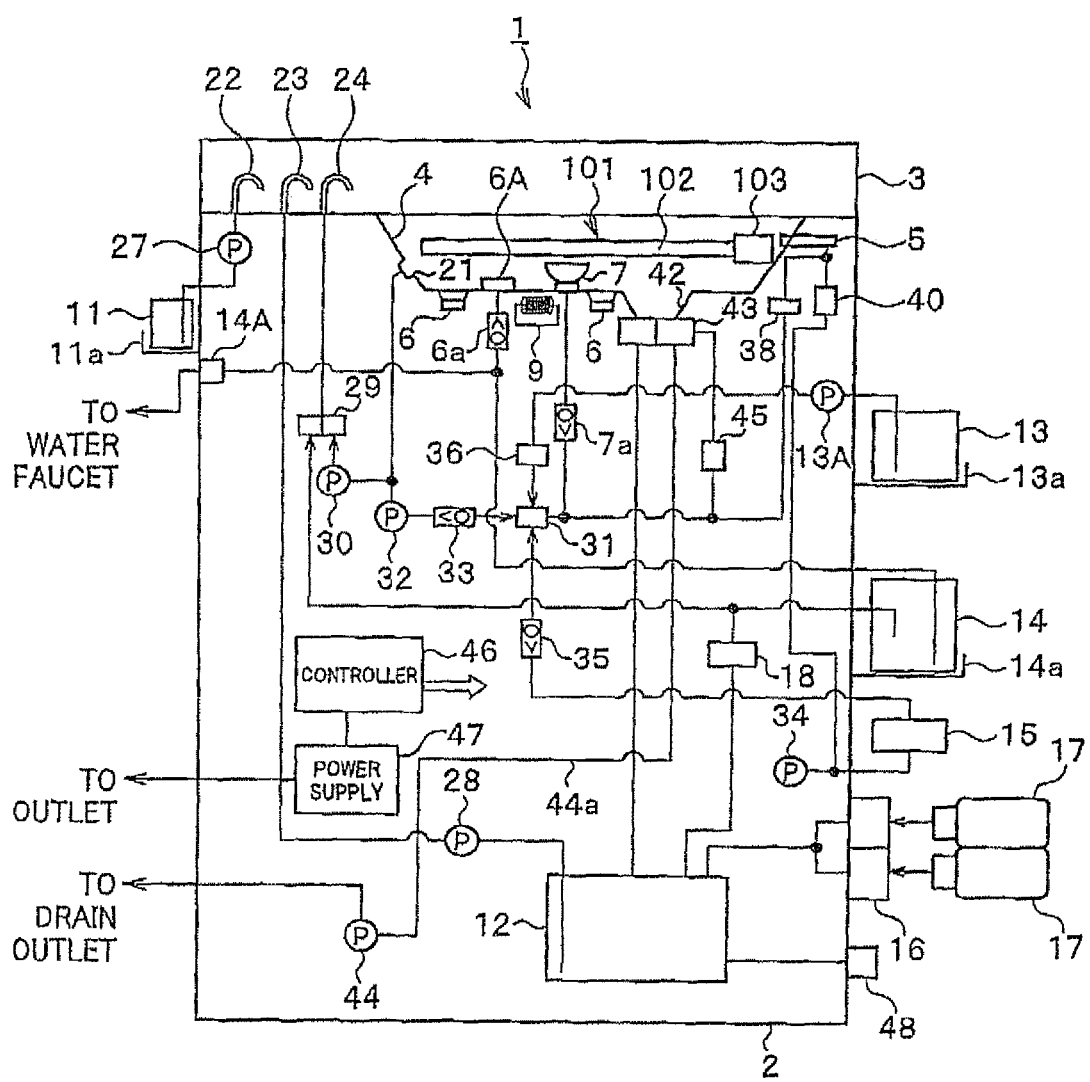
FIG. 2 is a view illustrating the configuration of the endoscope washer disinfector.

As shown in FIG. 2, the bottom 4A of the washing bath 4 is provided with a plurality of ultrasound transducers 6. These ultrasound transducers 6 function as means for generating vibration in liquid used for washing and disinfection of the endoscope 101. The bath bottom 4A has a central part on which the endoscope does not occupy the space. In this central part, a washing case 7 is disposed to accommodate various buttons which can be removed from the used endoscope 101. In addition, a heater 9 is disposed at the bath bottom 4A so that the liquid filled in the washing bath 4 is heated.

Within the apparatus main body 2, there are also arranged a washing-agent tank 11 in which a washing agent liquid is stored, a disinfecting-agent tank 12 in which a given dilutedconcentration disinfecting agent liquid is stored, an alcohol tank 13 in which alcohol is stored, and other elements. The other elements include a water filter 14 that filters tap water form a water faucet and an air filter 15. The disinfecting-agent tank 12 is fixed in the apparatus main body 2 and the washing-agent tank 11, alcohol tank 13, water tank 14, and air filter 15 are mounted on trays 11a, 13a-15a, respectively.

The apparatus main body 2 has a not-shown front door, so that when the door is opened, each of the trays 11a, 13a-15a can be drawn out from the apparatus main body 2 for refilling the liquid agents or exchanging parts. The water faucet is connected to a supply-duct disinfecting connector 6A via a check valve 6a, in which the connector 6A is secured to the bottom 4A of the washing bath 4.

Meanwhile since the disinfecting-agent tank 12 is fixedly arranged in the apparatus main body 12, refilling the disinfecting agent to the disinfecting-agent tank 12 needs to open the front door and connect a disinfecting-agent bottle 17 filled with the disinfecting agent to a bottle connector 16 fixed within the apparatus main body. Via a dilution valve 18, the tap water filtered by the water filer 14 is given to the disinfecting-agene tank 12. The tap water from the water faucet is fed into the water filer 14 by opening a water-supply valve 14A. Thus the disinfecting-agent tank 12 is able to store the disinfecting agent which is diluted to a predetermined concentration. FIG. 2 pictorially shows a state where the trays 11a, 13a-15a are drawn out from the apparatus main body.

The washing bath 4 is provided with a washing agent nozzle 22, a disinfecting agent nozzle 23, and a water supply/circulation nozzle 24, which are located at an upper part of a corner of the washing bath 4. The washing agent nozzle 22 communicates with the washing-agent tank 11 via a washing agent pump 27, while the disinfecting agent nozzle 23 communicates with the disinfecting-agent tank 12 via an agent pump 28. Further, the water supply/circulation nozzle 24 communicates selectively with the water filter 14 or a liquid-supply pump 30 via a three-way valve 29. In a switched state where the three-way valve 29 is switched to connect the water supply/circulation nozzle 24 to the water filter 14, the tap water filtered by the water filter 14 is discharged from the water supply/circulation nozzle 24.

In the oppositely switched state where the three-way valve 29 is switched to connect the water supply/circulation nozzle 24 to the flow pump 30, the wash water or disinfecting agent pooled in the washing bath 4 is discharged and circulated via a circulation outlet 21 formed at a given poison of the wall member of an accommodation recess provided in the washing bath 4. In the configuration shown in FIG. 2, though not shown, a high pressure nozzle is arranged between the water supply/circulation nozzle 24 and the three-way valve 29, and the high pressure nozzle is connected to a high pressure pump. Thus this high pressure nozzle is able to discharge liquid agents (such as tap water and washing water) in high pressure, which are similar to those from the water supply/circulation nozzle 24.

The liquids discharged from the high pressure nozzle and water supply/circulation nozzle 24 generates a flow of the liquid in the accommodation recess of the washing bath 4. This liquid flow makes it possible to wash and rinse the outer surfaces of the endoscope 101. The accommodation recess is also provided with a drain outlet in its bottom, as will be described.

The circulation outlet 21 is connected to a channel (CH) block 31 serving as a four-way selector valve, via a communication passage. In this communication passage, there are arrangements of a channel pump 32 and a check valve 33 in this order aligning from the circulation outlet 21. The check valve 33 checks the flow of the wash water or the disinfecting agent to the pump 32. By driving the pump 32, the wash water or disinfecting agent pooled in the accommodation recess is supplied to the channel bock 31. This channel block 31 also communicates with the filter 15 via a check valve 35. The check valve 35 checks the liquid (including the tap water, wash water, and disinfecting agent) not to make it flow to the air filter 15. The air filter 15 is connected to a compressor 34, in which air compressed by the compressor 34 is discharged to the channel block 31 via the filter 15.

Furthermore, the channel block 31 is produced to communicate with the alcohol tank 13 as well via a passage provided with a pump 13A and a valve 36 in this order aligning from the alcohol tank 13. Thus the alcohol preserved in the tank 13 is supplied by the pump 13A to the channel block 31 via the valve 36.

The various types of fluids supplied to the channel block 31, that is, the tap water, wash water, and disinfecting agent, are selectively fed to the fluid discharge device 5 via the channel block 31 and the vale 38 in each process for washing and disinfection. The fluid discharge device 5 receives the supply of air from the compressor 34 via a pressuring valve 40. Incidentally, the fluid discharge device 5 is secured to the side wall 4B of the washing bath 4.

A drain outlet 42 is arranged in the bottom 4A of the accommodation recess of the washing bath 4, and this drain outlet 42 is provided with a switching valve 43 that communicates with the disinfecting-agent tank 12. Selectively switching this valve 43 makes it possible to return the disinfecting agent pooled in the accommodation recess to the disinfecting-agent tank 12. The switching valve 43 also has a connection with an external drain outlet via a drain pipe 44a, so that the fluids, such as wash water and rinsing water, which are already used, are discharged outside. The drain pipe 44a is provided with a discharging pump 44 to suction the fluid pooled in the accommodation recess to send it outside the washer disinfector to the external drain outlet. The drain outlet 42 also has a connection with the channel block 31 through a passage, which is equipped with a bypass valve 45 on its way to the block 31.

The disinfecting agent stored in the disinfecting-agent tank 12, which is diluted at a predetermined concentration, is exchanged with new one every predetermined number of disinfecting steps. For this exchange of the disinfecting agent, a drain outlet 48 is arranged to connect the tank 12 to the outside, so that the disinfecting agent is discharged to the outside.

A controller 46 is provided within the apparatus main body 2 for controlling the foregoing various pumps, vales and devices every process among a series of predetermined processes including the washing, disinfecting, and drying processes. The controller 46 is provided with a computer system functioning as control means and connected with a power supply 47 receiving electric power from an external outlet.

Figure 3:
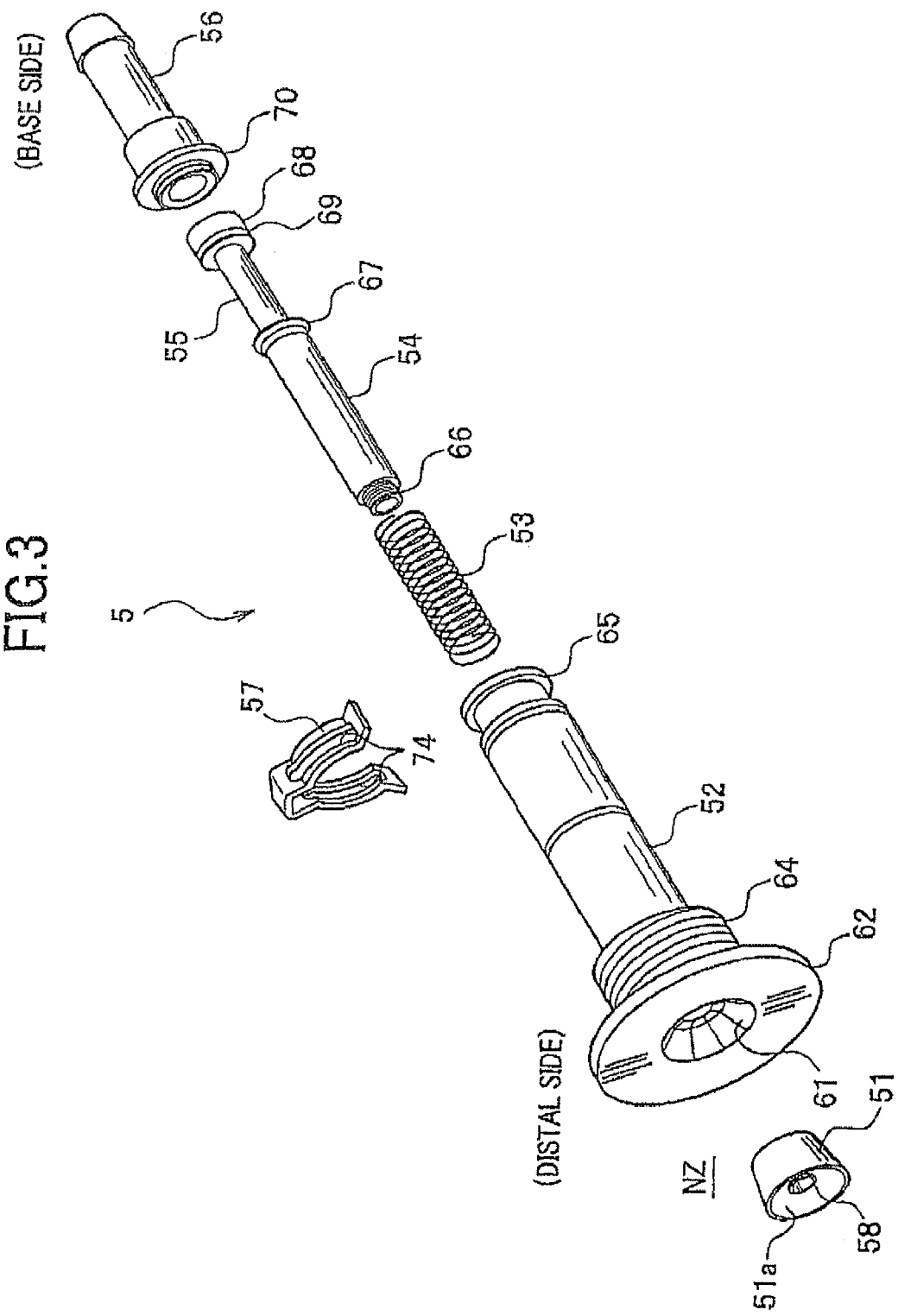
FIG. 3 is a disassembled perspective view showing a fluid discharge device installed in the endoscope washer disinfector.
Figure 8:
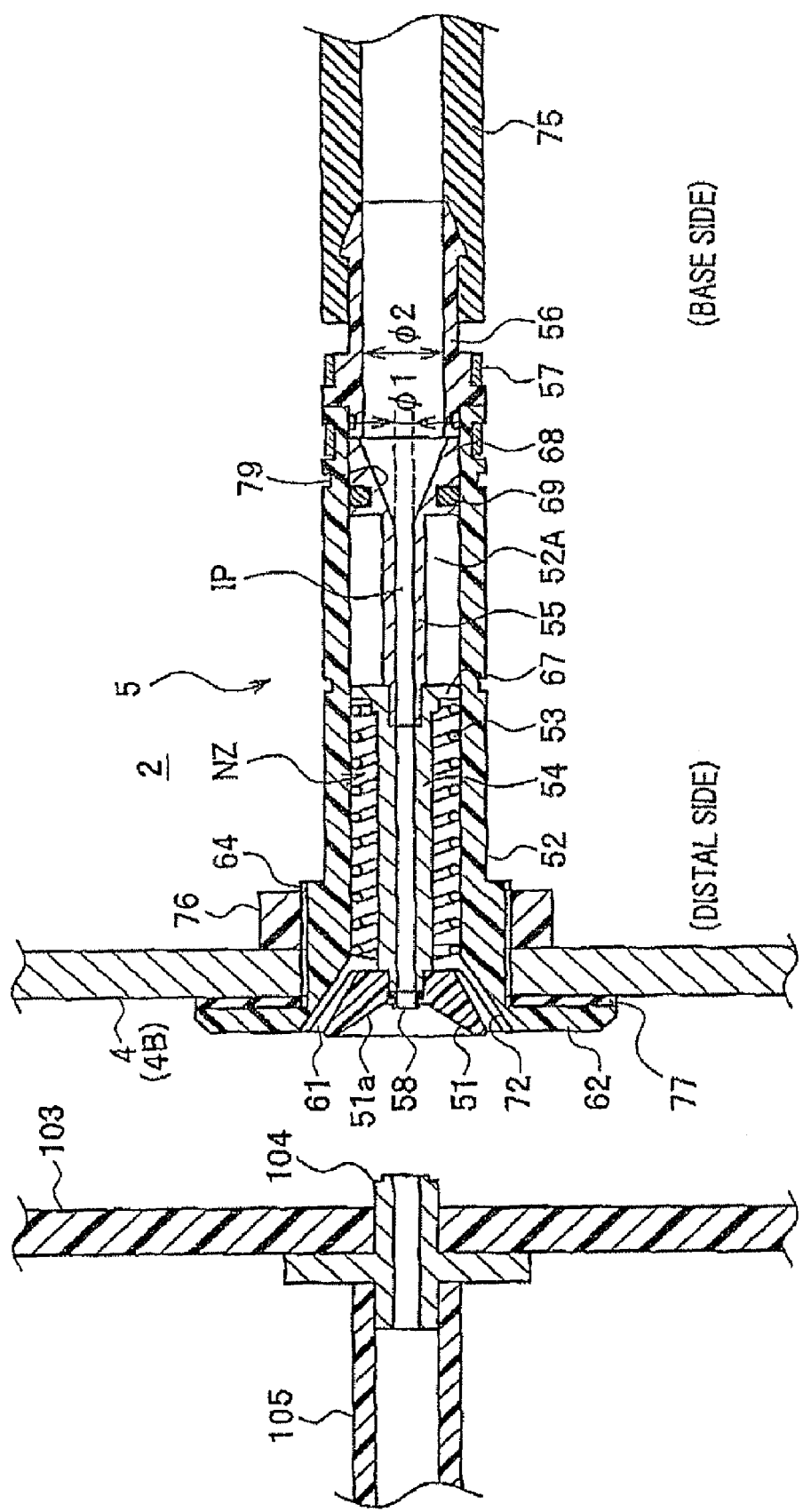
FIG. 8 is a cross section a state where the fluid discharge device is attached to the washing bath of the apparatus main body.

Referring to FIGS. 3 and 8, the fluid discharge device 5, which is arranged in the apparatus main body 2 so as to partly protrude in the washing bath 4, will now be detailed.

As shown in FIG. 3, the fluid discharge device 5 is equipped with a connection head 51, a first connection tube 52, a coil spring 53 which is an elastic member, a first nozzle tube 54, a second nozzle tube 55, a second connection tube 56, and a connection clip 57.

The connection head 51, which is made of non-metal materials such as resin, is an approximately cylindrical member with a mortar-like tapered surface 51a poisoned at the front thereof. The connection head 51 has a through-hole 71 formed along its axial direction. This through-hole 71 is positioned at the center in the plane perpendicular to the axial direction. A gasket 58, which has an approximate cylindrical shape and made of elastic material, is arranged in the though-hole 71 so that the gasket 58 slightly protrudes from the through-hole 71.

The first connection tube 52, which is made of non-metal materials such as resin, is a cylindrical member equipped with a flange 62, a threaded connecting portion 64 integral with the flange 62 and produced to have a threaded outer face; and a connection flange 65 positioned at the base end of the pipe 52.

Figure 4:
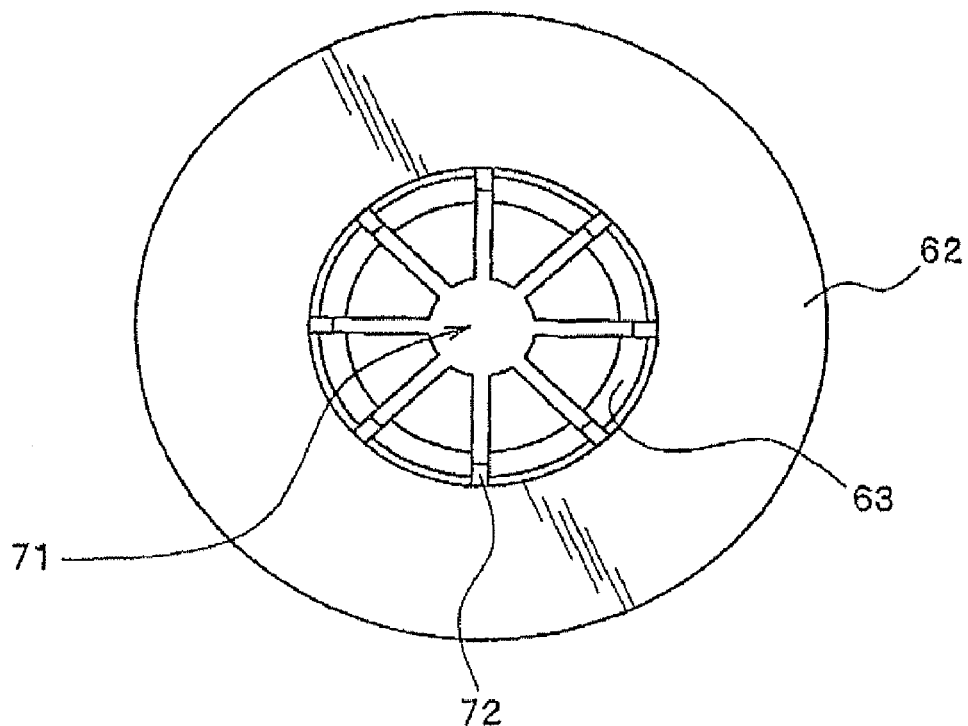
FIG. 4 is a frontal view showing the flange part of the fluid discharge device.
Figure 5:
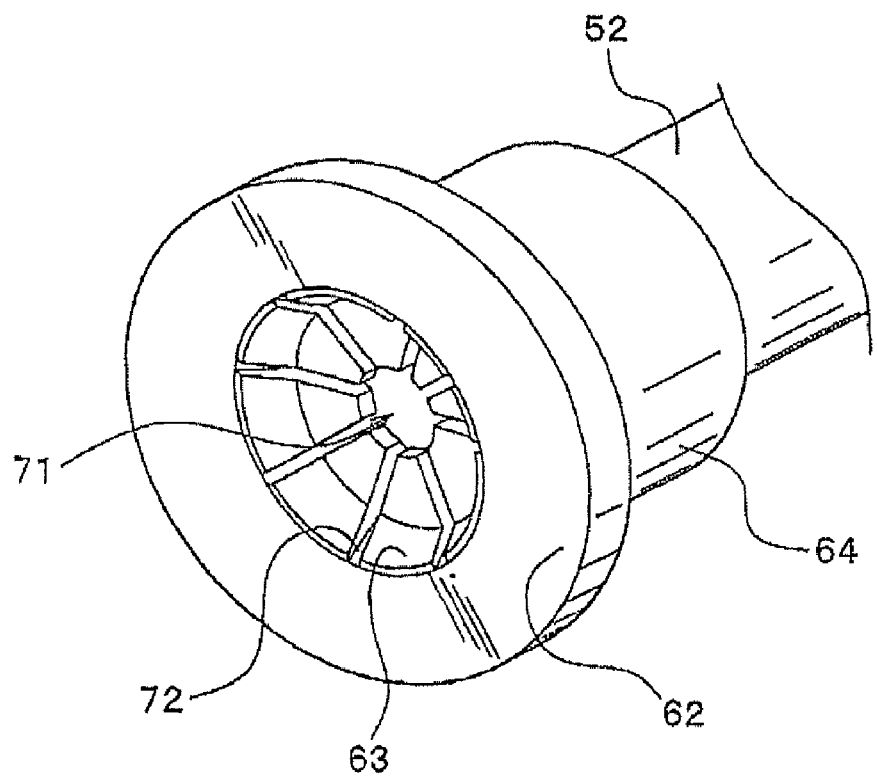
FIG. 5 is a perspective view showing the flange part of the fluid discharge device.

The mounting flange 62 has a recess 61 positioned at the front thereof and formed to be able to accommodate the connection head 51. As shown in FIGS. 4 and 5, this recess 61 is circular when viewed from the front and has a through-hole 71 positioned at the center in the plane perpendicular to the axial direction. The through-hole 71 is able to accommodate the nozzle tube 54 so as to go back and forth freely therethrough. In the recess 61 of the mounting flange 62, there are formed, by way of example, eight grooves 72 which radially extend from the center of the through-hole 71 at nearly equal angular intervals. The grooves 72 partially runs on the inner circumferential surface of the mounting flange 62 to reach the front thereof.

The threaded commenting portion 64 is able to be engaged with a nut, as will be described later, to allow the mounting flange 62 and the nut to tightly pinch the side wall of the washing bath 4, so that the fluid discharge device 5 can be mounted to the washing bath 4 securely. In the first connection tube 52, the first nozzle tube 54 and the second nozzle tube 55, which are shown in the disassembled form in FIG. 3, are placed using the coil spring 53.

The first nozzle tube 54 is made of metal and a screw portion 66 screwed with the base end of the connection head 51 and a flange portion 67 to receive a force. The first nozzle tube 54 is inserted through the spring 43, and this inserted assembly is inserted through the first connection tube 52. With the connection head 51 accommodated in the recess 61 of the mounting flange 62, the screw portion 66 is screwed with the connection head 51 so as to allow the connection head 51, spring 53 and first nozzle tube 54 loaded in the first connection tube 52.

The base end of the first nozzle tube 54 is subjected to screw-connection with the second nozzle tube 55 which is made of metal. This second nozzle tube 55 is also placed in the first connection tube 52. This second nozzle tube 55 has a base end equipped with a resisting member 68 (acting as a pressure reception part) which receives the pressure of the fluid flowing through first connection tube 52. The resisting member 68 has an approximate outer surface which is cylindrical. The outer surface of this resisting member 68 has a groove formed along the circumference thereof, and an O-ring 69 is embedded in the groove. The resisting member 68 will be detailed later.

The second connection tube 56, which is made of non-metal metals such as resin, has a distal end formed as a radially protruded connection flange 70, which is inserted into the first connection tube 52. A connection clip 57 is a metal plate member having curved portions with two engaging holes 74 formed on both sides.

Figure 6:
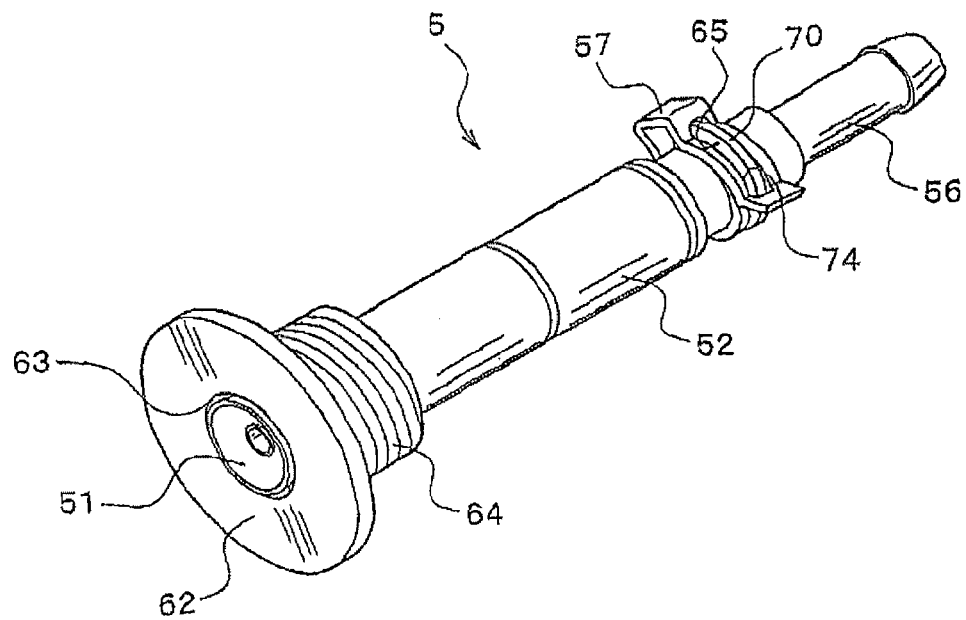
FIG. 6 is a perspective view showing the fluid discharge device.

These components are assembled into the fluid discharge device 5, as shown in FIG. 6. That is, the spring 53, first nozzle tube 54, and second nozzle tube 56 are arranged into the first connection tube 52, and the connection head 51 is connected to the first nozzle tube 54 in front of the first connection tube 52. After this, the first and second connection tubes 52 and 56 are connected to each other to compose an approximately cylindrical connector whose flange is realized by the distal end of the first connection tube 52. This connector has an approximately cylindrical internal passage 52A communicating between both ends in the axial direction thereof.

In addition, the combination of the connection head 51, first nozzle tube 54, and second nozzle tube 55 composes the nozzle NZ, through which an internal passage IP are formed therethrough in its axial direction.

In producing the nozzle NZ, the connection flanges 65 and 70 of the first and second connection tubes 52 and 56 are made to be contacted to each other, and the connection clip 57 is used to pinch the outer surfaces of the contacted connection flanges 65 and 70. The connection flanges 65 and 70 engage with the engaging holes 74 of the connection clip 57 to fixedly connect the first and second connection tubes 52 and 56. The connection clip 57 is designed to allow both contact surfaces of the connection flanges 65 and 70 to come in contact with each other in a predetermined pressing force, so that a sufficient watertight and airtight connection is secured.

Figure 7:
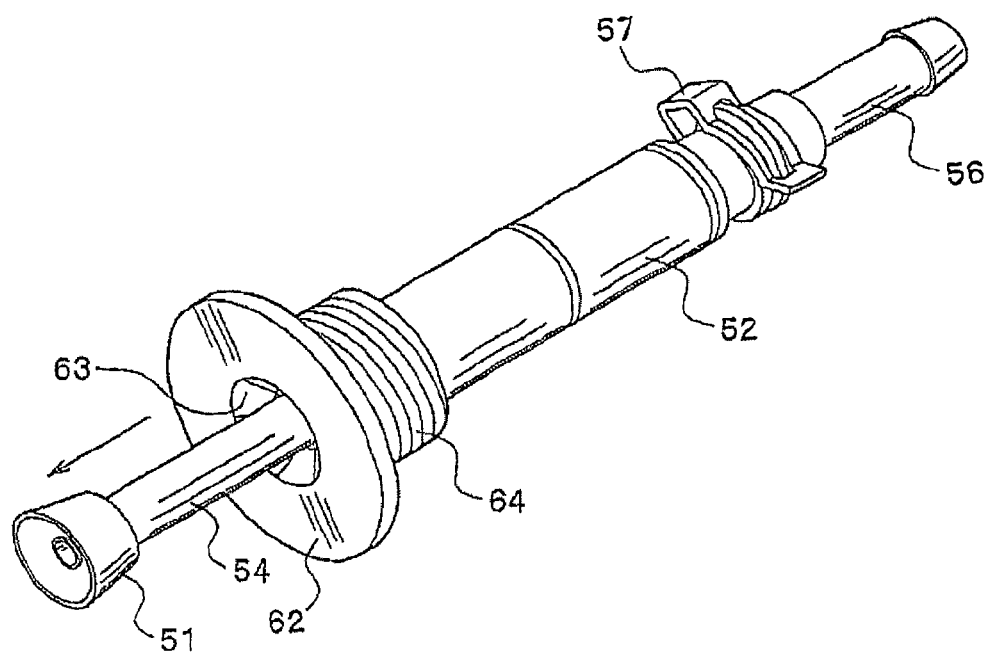
FIG. 7 is a perspective view showing a state where the nozzle of the fluid discharge device is extended.

In the assembled fluid discharge device 5 illustrated in FIG. 6, the first nozzle tube 54 receives the pressing force from the spring 53 toward the base end. In this state, the connection head 51, which is connected with the first nozzle tube 54, is accommodated in the recess 61 of the mounting flange 62 of the first connection tube 52. In addition, the connection head 51 can be pushed forward more than the first nozzle tube 54, as shown in FIG. 7, when a force acting against the pressing force of the spring 53 is applied to the first nozzle tube 54 from the base end side.

As shown in FIG. 8, the assembled fluid discharge device 5 is mounted in place to the side wall 43 of the washing bath 4. The position where the fluid discharge device 5 is mounted to the bath 4 is set such that the connection head 51 of the fluid discharge device 5 directly faces the opening (channel opening) 104 of each endoscopic channel 105 of the manipulating device 103 of the endoscope 101 positioned by the pins 4a in the washing bath 4. The channel opening 104 is made up of a metal member.

In mounting the fluid discharge device 5 to the side wall 4B of the washing bath 4, a rubber gasket 77 is placed between the mounting flange 62 and the washing bath 4 for maintaining the airtight and watertight performance. A nut 76 is then screwed with threaded connecting portion 64 of the first connection tube 52 from the rear side of the bath 4, whereby the fluid discharge device 5 is installed to the washing bath 4. A tube 75 is connected to the second connection tube 56 to supply the device 5 with the various types of liquid for the washing and disinfection work.

Specifically, the first and second connection tubes 52 and 56, which compose the main body of the fluid discharge device 5, provides a single inner passage whose one axial end is opened from the side wall 4B of the washing bath 4 and whose other axial end is coupled with the fluid supply tube 75. This allows the first and second nozzle tubes 54 and 55, which compose the nozzle NZ, to slide in along only the inner passage provided by the device main body, without touching the washing bath 4. Thus, the fluid supplied through the tube 75 is discharged from the fluid discharge device 5 into the washing bath 4. In this fluid discharge device 5, the fluid is prevented from leaking into the apparatus main body 2, even if sliding motions of the nozzle NZ causes deterioration in the gasket and O-ring.

Furthermore, the resisting member 68 formed at the base end of the second nozzle tube 55 has an outer diameter which is almost the same as the inner diameter of the inner cylindrical through-hole of the first connection tube 52. That is, the second nozzle tube 55 is slidable in along the inner through-hole of the first connection tube 52, with an airtight and watertight performance kept by both the O-ring 69 on the resisting member 69 and the outer circumferential surface of the member 69 itself.

The resisting member 68 has a recess 79 whose surface is conular and tapered to be narrower in diameter as advancing toward the distal end of the tube 55. The recess 79 is formed to communicate with the inner passage of the second nozzle tube 55 itself. The inner passage of the second nozzle tube 55 also communicates with the inner passage of the first nozzle tube 54 and extends outside through the gasket 58 of the connection head 51. The diameter $\phi 1$ of the inner passage of the second nozzle tube 55 is smaller than that $\phi 2$ of the second connection tube 56 ($\phi 1 < \phi 2$). This difference between the inner diameters enables the resisting member 68 to have a stronger resistance against a flow of the fluid and act as a pressure receiving member to receive a pressing force of the fluid. The strength of the resistance (i.e., pressure) can be adjusted by adjusting the difference in the diameters. The larger the difference, the greater the resistance. The recess 79 has the tapered inner surface, thereby making it easier to pass a washing brush.

In the endoscope washer disinfector 1 according to the present embodiment, a used endoscope 101 accommodated in the washing bath 4 is subjected to each of the washing, rising, disinfecting and drying processes (steps) which are previously programmed.

Figure 9:
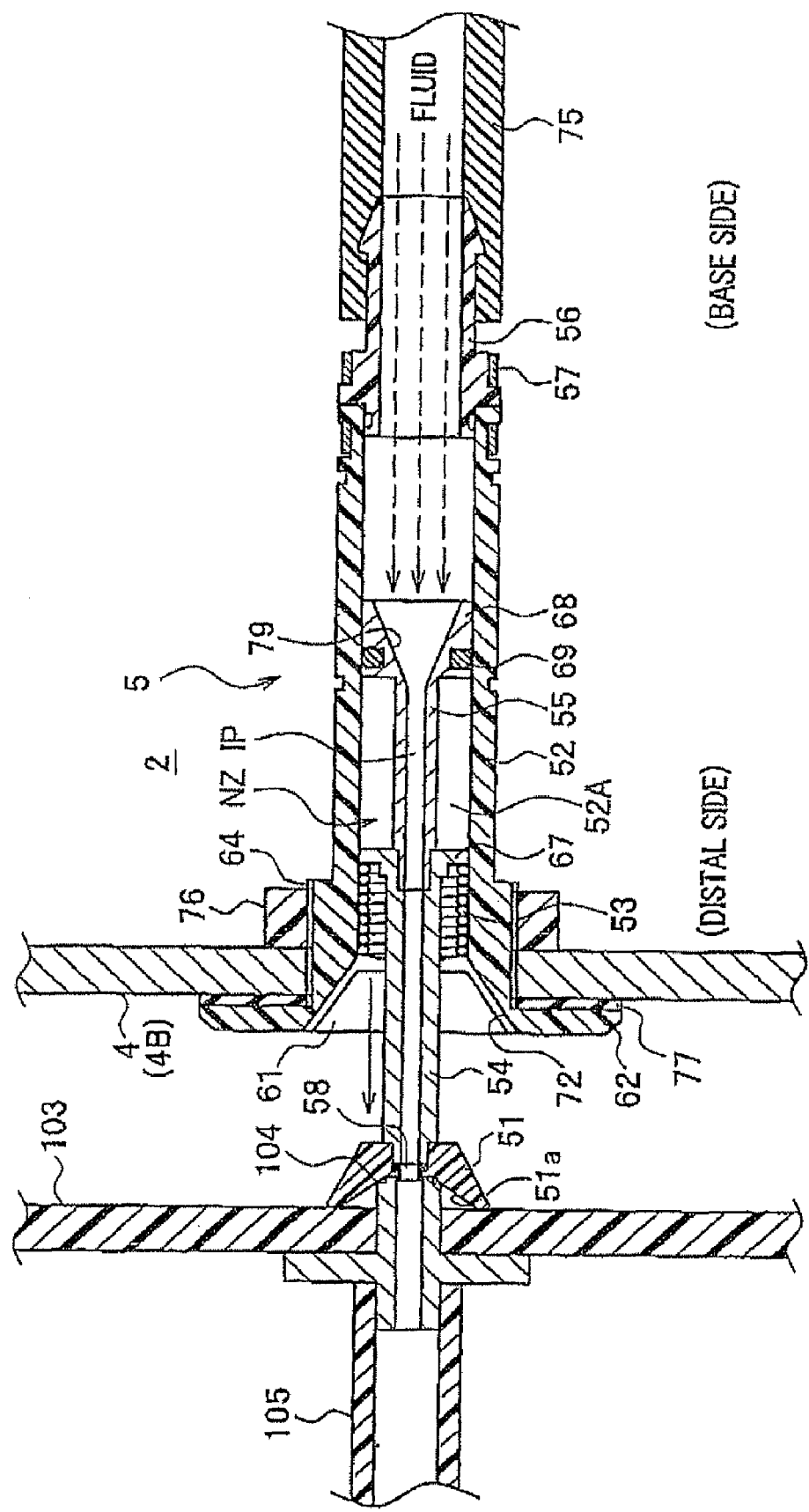
FIG. 9 is a cross section that explains the operations of the fluid discharge device.

Referring to FIGS. 8 and 9, how the fluid discharge device 5 operates to supply the liquid fluid (including washing agent, disinfecting agent, rising water, air and alcohol) into each channel of the endoscope 101 in each process for the washing and disinfection.

In a state where there is no fluid supplied from the apparatus main body 2 via the tube 75, the fluid discharge device 5 provides a positional state shown in FIG. 8. Namely, the flange portion 67 of the first nozzle tube 54 receives the pressing force of the spring 53, resulting in that the first and second nozzle tubes 54 and 55, that is, the nozzle NZ, is pushed away at the maximum position on the base end side within the first connection tube 52. In this state, the connection head 51 connected with the first nozzle tube 54 is accommodated in the recess 61 of the mounting flange 62 of the first connection tube 52.

When each process for the washing and disinfection work for the endoscope 101 begins, the fluid begins to be supplied to the fluid discharge device 5 via the tube 75 from the apparatus main body 2. In response to starting the fluid supply, as shown in FIG. 9, the resisting member 68 of the second nozzle tube 55, that is, the nozzle NZ, receives pressure from the fluid flow, so that the nozzle NZ is pushed forward so as to allow the first nozzle tube 54 protrudes, together with the connection head 51, from the recess 61 of the mounting flange 62.

In this way, the fluid flowing through the fluid discharge device 5 gives pressure to the resisting member 68. That is, when the flow passes along the recess 79 of the second nozzle tube 55, the pressure, that is, a pushing force is forcibly applied to the resisting member 68, due to the fact that the difference is given to the inner diameters φ1 and φ2 (φ1<φ2), as explained in FIG. 8. This pushing force overcomes the pressing force of the spring 53.

The pressure applied to the resisting member 68 should be larger than the pushing force from the spring 53. For this purpose, the fluid supply pressure decided on the specifications of the various pumps and compressor and the pushing force of the spring 53 are set to appropriate values.

When the nozzle NZ is pushed forward by the pressure of the fluid, the connection head 51 of the nozzle NZ is forced to quickly extend from the recess 61 of the mounting flange 62 toward the manipulating device 103 of the endoscope 101 accommodated in place in the bath. Thus, in a short time, the connection head 51 forcibly comes in contact with each channel opening 104 of the manipulating device 103 to be connected therewith rigidly.

When such a connection is realized, the gasket 58 of the connection head 51 is closely and forcibly touched to the channel opening 104. Thus, the fluid passing through the first and second nozzle tubes 54 and 55 is then fed into the cannel 105 from its opening 104.

During the step in which the connection head 51 advances to be connected to the channel opening 104, the tapered surface 51a of the connection head 51 acts as a guide surface to guide the channel opening 104 in such a manner that the channel opening 104 is directed toward the inner passage IP of the first nozzle tube 54, which is positioned at the central part of the connection head 51 when viewing the front thereof. Hence even if the manipulating device 103 of the endoscope 101 is slightly shifted from the exact position within the area defined by the pins 4a in the washing bath 4, the connection head 51 can securely be connected to the channel opening 104.

On completion of the fluid supply to each channel 105 of the endoscope 101 is finished in each process, the pressure from the fluid flow to the resisting member 68 will disappear. Hence the pressing force of the spring 53 applied to the flange portion 67 of the first nozzle tube 54 becomes dominant, thus pushing back the first and second nozzle tubes 54 and 55, that is, the nozzle NZ, toward the base end side within the first connection tube 52. Accordingly, the connection head 51 of the nozzle NZ releases the connection with the channel opening 104 and returns to the initial position in the recess 61 of the mounting flange 62.

In this way, in the endoscope washer disinfector 1 of the present embodiment, the pressure of flow of the fluid (such as rinsing water, washing agent (wash water), disinfecting agent, alcohol, and air) to be supplied to the endoscopic channels 105 of the endoscope 101 can be utilized for connecting the nozzle NZ, which is mainly composed of the connection head 51 and the first and second nozzle tubes 54 and 55. A further advantageous point is that the connection is carried out in a detachable and watertight/airtight manner.

Accordingly, without installing electrical configurations such as motors, the automatic connection and disconnection of the nozzle NZ to and from the endoscopic channel openings 104 can be achieved by employing a mechanically-simple pressing mechanism which operates on the fluid flow pressure. This eliminates the necessity of using the electrical configurations and control systems for moving the nozzle NZ back end forth, being advantageous in lowering parts cost.

Moreover, as understood from FIG. 9 as well, the first and second nozzle tubes 54 and 55 are allowed to move within the first connection tube 52. Thus there is no leakage of the supplied fluid into the apparatus main body 2, and the fluid supplied from the apparatus main body 2 to the fluid discharge device 5 though the tube 75 is circulated via only the channels 105 of the endoscope 101 and the washing bath 4.

The mounting flange 62 of the first connection tube 52 is secured to the side wall 4B of the washing bath 4 with the gasket 77 inserted therebetween. Since there are no parts in this configuration after securing the tube 52 to the washing bath 4, the gasket 77 gives a sufficing air and water sealing performance between the washing bath 4 and the apparatus main body 2.

There is another advantage resultant from deterioration of the O-ring 69, which is placed on the resisting member 68 of the second nozzle tube 55. This O-ring 69 will cause abrasion due to the slide motions of the second nozzle tube 55. The first and second connection tubes 52 and the tube 75 is closed watertightly, so that even if the O-ring deteriorates, no leakage of the fluid into the apparatus main body 2 will occur. Thus, malfunctions on account of the leakage, such as earth leakage from internal electrical components in the apparatus main body 2, will be avoided.

In this way, the fluid discharge device 5 is sufficiently closed in terms of its sealing structure, so that the O-ring 69 may omit from the resisting member 68. That is, it is not always required to load the O-ring 69 on the resisting member 68, as long as the resisting member 68 receives the fluid pressure to move the nozzle NZ. With no O-ring, there is caused no friction on the inner surface of the first connection tube 52, whereby the nozzle NZ, i.e., the connection head 51 and the first and second nozzle tubes 54 and 55 can move smoothly.

During each of the processes required for washing and disinfecting the endoscope 101, each of the rinsing water, washing agent (wash water), and disinfecting agent is pooled in the washing bath 4. Hence, in the fluid discharge device 5, the fluid flows into the first connection tube 52 from the recess 61 of the mounting flange 62. However, in the present embodiment, as shown in FIGS. 4 and 5, the recess 61 is formed to communicate with the outside through the plural grooves 72 formed through the plate member partitioning the recess 61. Thus, when the level of the fluid in the washing bath 4 is lowered, the fluid flowed in the device 5 is discharged naturally into the washing bath 4 through the grooves 72.

Further, since the connection head 51 is made of resin material, the metal-made channel openings 104 can be prevented from being damaged. Even when there occurs damage of deterioration of the connection head 51 due to connection actions to the channel openings 104, the connection head 51 and the first and second nozzle tubes 54 and 55 are detachable to and from the device 5, so that the nozzle NZ can be replaced easily by a new one. In addition to the deterioration of the connection head 51, the spring 53 and/or O-ring 69 may deteriorate. In such a case, the connection head 51 is first removed from the first nozzle tube 54, and then pulled out from the first connection tube 52. By disassembling the device 5 in this way, all the connection head 51, first nozzle tube 54, and second nozzle tube 55, the spring 53, or only the O-ring 69 can be replaced by new ones.

Figure 10:
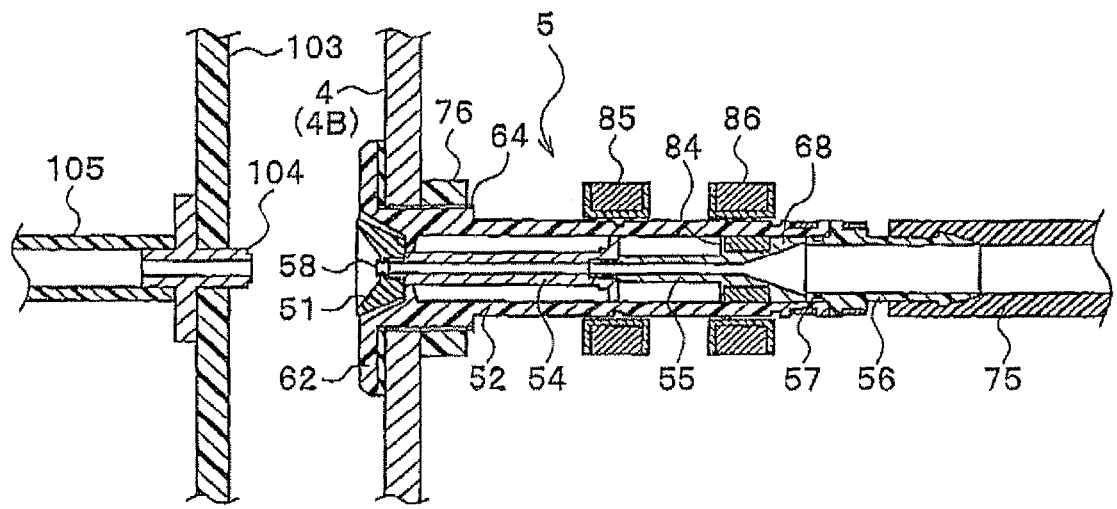
FIG. 10 is, according to a modification of the present invention, a cross section showing a state where the fluid discharge device is attached to the washing bath of the apparatus main body.
Figure 11:
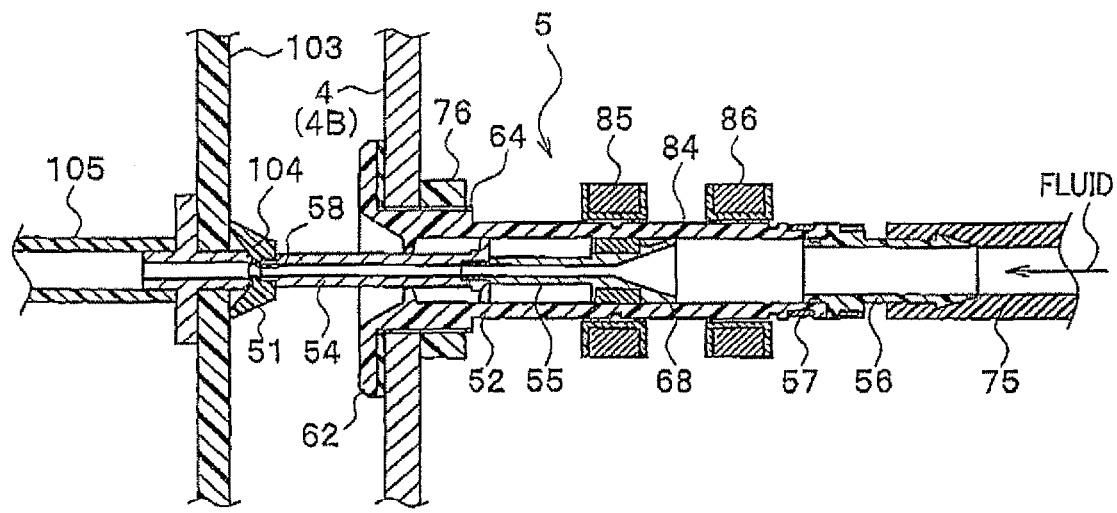
FIG. 11 is a cross section that explains the operations of the fluid discharge device according to the modification.

The foregoing fluid discharge device 5 can be modified into another form shown in FIGS. 10 and 11, in which the nozzle NZ is designed to move by a solenoid driving mechanism.

Specifically, as shown in FIGS. 10 and 11, a magnetic member 84 is attached to the resisting member 68 of the fluid discharge device 5 and this magnetic member 84 is magnetically pulled and pushed to move the device 5. For such pulling operations, magnetic generators 85 and 86 are disposed around the outer circumferential surface of the first connection tube 52 at intervals in the axial direction thereof.

Of the two magnetic generators 85 and 86, the front-side one, i.e., the magnetic generator 85 is disposed for pushing forward the nozzle NZ, i.e., the connection head 51 and the first and second nozzle tubes 54 and 55. Meanwhile the rear-side magnetic generator 86 is for pulling back the nozzle NZ.

In other words, before the connection head 51 is driven to be connected to the channel opening 104 of the endoscope 101 as shown in FIG. 10, the rear-side magnetic generator 86 is switched "ON" and the fronts-side magnetic generator 85 is kept at its "OFF" state. Meanwhile, when the connection head 51 is connected to the channel opening 104 as shown in FIG. 11, both generators 85 and 86 are driven in the opposite way as the above. That is, the front-side generator is switched "ON" and the rear-side one 86 is kept to its "OFF" state.

The magnetic driving mechanism will not be limited to the above magnetic generators 85 and 86 that selectively generate the magnetic pulling force acting on the magnetic pole different from the magnetic member 84. An alternative is that the generators 85 and 86 selectively generate a magnetic repelling force acting on the magnetic pole which is the same as that of the magnetic member 84, whereby a pushing force is generated to drive the nozzle NZ on the repelling forces.

The magnetic generators 85 and 86 are structured into a solenoid magnetic mechanism. Applications of this mechanism is not limited to driving the nozzle NZ in order to supply the fluid to the channels 105, but can be carried out as another form. With the fluid supplied to the fluid discharge device 5, the nozzle NZ can be controlled such that the nozzle is connected to the channel opening 104. Alternatively, with the fluid not supplied to the fluid discharge device 5, the nozzle NZ can be controlled such that the nozzle is retained to be connected to the channel opening 104.

In the above mechanism, the rear-side magnetic generator 86 is arranged to pull back the nozzle NZ, whereby it is not needed to arrange the foregoing spring 53 to push the nozzle backward. Instead of this, the combination of the spring 53 and only the front-side pushing magnetic generator 85 is sufficient, with rear-side magnetic generator 86 omitted from the mechanism. In this mechanism, only controlling the ON/OFF states of the generator 85 makes it possible to move the nozzle NZ back and forth in the same manner as described before. Moreover, only the rear-side pulling-back magnetic generator 86 may be arranged alone to use the repelling force on the same magnetic pole, thereby allowing the nozzle NZ to move in response to the ON/OFF operations of the generator 86.

In addition, the resisting member of the nozzle NZ according to the present invention may be modified into another form, not limited to the foregoing resisting member 68 with the tapered inner circumferential surface. Alternatively, another resisting member can be produced as a cylindrical member with a cylindrical through-hole formed in its axial direction and a toric end face acting as a pressure reception part perpendicular to the flow of the fluid. It is enough for the resisting member to cause an appropriate resistance when receiving the fluid flow, in order to overcome the pressing force of the spring 53.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. An endoscope washer disinfector comprising:
   a bath comprising a mounting plane on which an endoscope provided with a duct necessary for endoscopic therapy is mounted and a wall member that surrounds the mounting plane, wherein the mounting plane provides a given position at which the endoscope is positioned;
   a connector having i) two ends consisting of one end located to penetrate through the wall member and to be secured watertightly to the wall member such that the one end faces an opening of the duct of the endoscope mounted at the given position in the bath and the other end receiving fluid for washing and disinfecting the endoscope and ii) an inner passage that communicates between both ends; and
   a nozzle inserted watertightly and movably in the connector along the inner passage thereof and moved toward the one end of the connector to protrude from the one end to realize a watertight and detachable connection with the opening of the duct so as to supply the fluid to the duct when the fluid is supplied from the fluid source.

2. The endoscope washer disinfector of claim 1, comprising an elastic member that i) makes the connector contain the nozzle in the inner passage thereof, when the fluid source refrains from supplying the fluid to the inner passage of the connector, and ii) uses a pressing force of the fluid to move the nozzle toward the one end of the connector so that the nozzle protrudes from the one end to be connected watertightly and detachably to the opening of the duct, when the fluid source supplies the fluid to the inner passage of the connector.

3. The endoscope washer disinfector of claim 2, wherein the elastic member is disposed in the inner passage of the connector to allow the nozzle to be inserted in the elastic member and formed to have two ends that consist of one end fixedly secured to the inner passage and the other end engaged with an outer surface of the nozzle.

4. The endoscope washer disinfector of claim 2, wherein
   the inner passage of the connector provides a first inner diameter located at part of the inner passage;
   the nozzle that has both end in an axial direction thereof, an inner passage communicating between both axial ends, and a pressure reception part receiving the pressing force of the fluid supplied from the fluid source; and
   the inner passage of the nozzle has a second inner diameter smaller than the first inner diameter.

5. The endoscope washer disinfector of claim 4, wherein the pressure reception part of the nozzle is located to be next to the part of the inner passage of the connector, which has the first inner diameter, in the axial direction such that the pressure reception part comes after the part of the inner passage of the connector in a direction in which the fluid is supplied, whereby the pressure reception part is allowed to work as a resisting member receiving the pressing force of the fluid.

6. The endoscope washer disinfector of claim 5, comprising an O-ring inserted between an outer circumferential surface of the pressure reception part and an inner circumferential surface of the connector so as to allow the nozzle to move back and forth.

7. The endoscope washer disinfector of claim 5, wherein the pressure reception part has an approximately conular tapered surface that shrinks in diameter from the part of the connector, which has the first inner diameter, to the inner passage of the nozzle, which has the second inner diameter.

8. The endoscope washer disinfector of claim 5, wherein the nozzle comprises a connecting portion made of non-metal material and formed to be connected watertightly and detachably to the opening of the duct.

9. The endoscope washer disinfector of claim 8, wherein the connecting part has a guide surface guiding an opening of the duct to a central part of an end face of the nozzle, when the connecting part is connected to the opening of the duct, the guide surface extending in an inner diameter thereof toward the opening.

10. The endoscope washer disinfector of claim 8, wherein the one end of the connector, which faces the opening of the duct, has a flange with a recess which allows the connecting part of the nozzle to be accommodated therein, and the recess has at least one groove to discharge fluid.

* * * * *